United States Patent [19]

Mills, Jr. et al.

[11] Patent Number: 6,150,102
[45] Date of Patent: Nov. 21, 2000

[54] METHOD OF GENERATING NUCLEIC ACID OLIGOMERS OF KNOWN COMPOSITION

[75] Inventors: Allen P. Mills, Jr., Chatham; Bernard Yurke, Plainfield, both of N.J.

[73] Assignee: Lucent Technologies Inc., Murray Hill, N.J.

[21] Appl. No.: 09/078,761

[22] Filed: May 15, 1998

Related U.S. Application Data

[63] Continuation-in-part of application No. 09/018,248, Feb. 3, 1998.

[51] Int. Cl.[7] .............................. C12Q 1/68; C12P 19/34; G01N 15/06; G01N 27/00; B32B 19/02

[52] U.S. Cl. .......................... 435/6; 435/91.1; 435/91.2; 422/68.1; 422/50; 422/63; 422/82.01; 422/82.02; 422/82.12; 422/131; 422/138

[58] Field of Search ........................... 435/6, 91.1, 91.2; 422/68.1, 50, 63, 82.01, 82.02, 82.12, 131, 138

[56] References Cited

U.S. PATENT DOCUMENTS

| | | | |
|---|---|---|---|
| 5,412,087 | 5/1995 | McGall et al. | 536/24.3 |
| 5,445,934 | 8/1995 | Fodor et al. | 435/6 |
| 5,503,980 | 4/1996 | Cantor | 435/6 |
| 5,561,071 | 10/1996 | Hollenberg et al. | 437/1 |
| 5,605,662 | 2/1997 | Heller et al. | 422/68.1 |

OTHER PUBLICATIONS

Corn, DNA Computing Overview, last modified Mar. 13, 1998, <http//www.corninfo.wisc.edu/writings/DNAoverview.html>).

Pall Ultrafine Filtration Corporation, "Protocols for DNA and RNA Transfer, DNA Electrotransfer, and Protein Transfer to Biodyne, A Nylon Membranes," 1983, East Hills, NY, pp. 3–5, and 14–15.

A. Marshall et al., "DNA chips: An array of possibilities," Nature Biotechnology, vol. 16, Jan. 1998, pp. 27–31.

Graham Ramsay, "DNA chips: State-of-the art", Nature Biotechnology, vol. 16., Jan. 1998, pp. 40–44.

Leonard M. Adleman, "Molecular Computation of Solutions to Combinatorial Problems", Science, vol. 226, Nov. 11, 1994, pp. 1021–1024.

John S. Oliver, "Matrix Multiplication with DNA", Journal of Molecular Evolution, (1997) 45: 161–167.

Richard J. Lipton, "DNA Solution of Hard Computational Problems", Science, vol. 268, Apr. 28, 1995, pp. 542–545.

Frank Guarnieri, et al., "Making DNA Add", Science, vol. 273, Jul. 12, 1996, pp. 220–223.

Natalie Milner et al., "Selecting effective antisense reagents on combinatorial oligonucleotide arrays", Nature Biotechnology, vol. 15, Jun. 15, 1997, pp. 537–541.

Ann Caviani Pease et al., "Light-generated oligonucleotide arrays for rapid DNA sequence analysis", Proc. Natl. Acad. Sci. USA, vol. 91, pp. 5022–5026. May 1994.

Glenn H. McGall, et al., "The Efficiency of Light-Directed Synthesis of DNA Arrays on Glass Substrates", Journal of the American Chemical Society, vol. 119, No. 22, Jun. 4, 1997 pp. 5081–5090.

Susan L. Berent et al., "Comparison of Oligonuleotide and Long DNA Fragments as Probes in DNA and RNA Dot, Southern, Northern, Colony and Plaque Hybridizations", BioTechniques, May/Jun. 1985, pp. 208–220.

(List continued on next page.)

Primary Examiner—Jezia Riley

[57] ABSTRACT

The present invention is directed to a method for providing oligonucleotides or oligonucleotide analogs having known subunit sequences in which the desired oligomers are released from selected storage sites in one, two, or three dimensions, on a substrate by locally denaturing double-stranded complexes at the storage sites containing the desired oligomers. The released oligomers are useful in schemes for determining solutions to mathematical problems, in methods wherein hybridizing oligomers are used to encrypt and transmit data, in diagnostic and screening assay methodologies, and as primers or building blocks for synthesizing larger polynucleotides.

17 Claims, 6 Drawing Sheets

OTHER PUBLICATIONS

Chad A. Mirkin et al., "A DNA–based method for rationally assembling nanoparticles into macroscopic materials," Nature, vol. 382, Aug. 15, 1996, pp. 607–609.

L.E. Morrison and L. M. Stols, "Sensitive fluorescence–based thermodynamic and kinetic measurements of DNA hybridization in solution", *Biochemistry 32* (1993) 3095–3104.

M. Chee, et al., "Accessing genetic information with high–density DNA arrays", Science 274 (1996) 610–614.

M. J. Kozal et al., "Extensive polymorphisms observed in HIV–1 clade B protease gene using high–density oligonucleotide arrays", Nature Medicine 2 (1996) 753–759.

D. I. Stimpson et al., "Real–time detection of DNA hybridization and melting on oligonucleotide arrays by using optical wave guides", Proc. Nat Acad. Sci. USA 92 (1995) 6379–6383.

E.L. Sheldon et al., "Matrix DNA hybridization", Clinical Chemistry 39 (1993) 718–719.

Charles R. Cantor and P.R. Schimmel, *Biophysical Chemistry*, Part III (Freeman, New York, 1980) pp. 1217 & 1226–1234.

Ted Kamins, *Polycrystalline Silicon For Integrated Circuit Applications*, Kluwer Academic Publishers, 1988, pp. v–xii and 155–174.

Sambrook, J., et al., *Molecular Cloning, A Laboratory Manual*, from Chapter 11, "Synthetic Oligonucleotide Probes" (Cold Spring Harbor Laboratory Press, 1989), pp. 11.2–11.19, 11.45–11.49, and 11.52–1.61.

Francisco J. Ayala, et al., *Modern Genetics*, Second Edition, from Chapter 9, "DNA Manipulation" (Benjamin/Cummings, Menlo Park, CA, 1984), pp. 262–267 and Appendix 1.

R. J. Britten et al., "Repeated Sequences in DNA", Science, 161 (No. 3841), Aug. 9, 1968, pp. 529–540.

R. J. Britten, et al., "Analysis of Repeated DNA Sequences By Reassociation", Methods In Enzymology, vol. 29, Part E (1974) pp. 363–418.

James G. Wetmur, et al., "Kinetics of Renaturation of DNA", J. Molecular Biology 31 (1968) 349–370.

METHOD OF GENERATING NUCLEIC ACID OLIGOMERS OF KNOWN COMPOSITION

CROSS-REFERENCES TO RELATED APPLICATIONS

This application is a continuation-in-part of U.S. application Ser. No. 09/018,248 filed Feb. 3, 1998.

FIELD OF THE INVENTION

This invention pertains to a method for providing oligomers of known subunit sequence which hybridize specifically to DNA and RNA having complementary nucleotide sequences, in which the desired oligomers are released from selected storage sites on a substrate by locally denaturing double-stranded complexes at the storage sites containing the desired oligomers. The released oligomers are oligonucleotides or oligonucleotide analogs, and are useful in schemes for determining solutions to mathematical problems, in methods wherein hybridizing oligomers are used to encrypt and transmit data, in diagnostic and screening assay methodologies, and as primers or building blocks for synthesizing larger polynucleotides. The present invention also features providing oligomers having desired subunit sequences from a device comprising a substrate supporting an array of oligomer-storing depot sites made by a novel method for the synthesis of DNA arrays which utilizes local melting of hybridized DNA and produces a set of substrate-attached oligomers of known subunit sequence. The present invention has applications in the fields of molecular computation, biochemistry, molecular biology, pharmacology, medical diagnostic technology, and data encryption and transmission.

BACKGROUND OF THE INVENTION

All publications and patent applications herein are incorporated by reference, fully as if each individual publication or patent application was specifically and individually indicated to be incorporated by reference.

Various strategies for finding solutions to mathematical problems have been devised which use sets of DNA oligonucleotides having selected length and sequence properties. For example, DNA-based methods are developed for solving a Hamiltonian path problem (Adleman, Science, 1994, Vol. 266, pages 1021–3), a "satisfaction" problem (Lipton, Science, 1995, Vol. 268, pages 542–5), and for performing addition (Guarnieri et al., 1996, Science, vol. 273, pages 220–223) and matrix multiplication (Oliver, J. Molecular Evolution, 1997, Vol. 45, pages 161–7 ) of non-negative numbers. Each computation requires a set of oligonucleotides having properties tailored to the problem to be solved. Thus, a rapid and efficient method for providing custom sets of oligonucleotides having selected sequence and length properties is essential for efficient application of DNA-based computation methods.

The present ability to detect oligonucleotides that are bound in a sequence-specific manner to discrete sites of a hybridization array permits the use of oligonucleotides to encrypt and transmit data; a use which, like nucleic acid computation, requires numerous custom sets of oligonucleotides having particular sequences and hybridization properties.

Oligonucleotides are also used as hybridization probes to detect specific nucleic acid sequences in DNA and RNA samples immobilized on a variety of filter and solid supports, as in DNA and RNA Dot, Southern, and Northern blots, and in colony and plaque hybridization assays. These methodologies are widely used in the isolation and cloning of specific nucleic acids, and the diagnosis of disease caused by pathogens and genetic mutations (Berent et al., BioTechniques, issue of May/June 1985, pages 208–20; and J. Sambrook, E. F. Fritsch, and T. Maniatis, Molecular Cloning, A Laboratory Manual, Cold Spring Harbor Laboratory Press, Cold Spring Harbor, New York, 1989, Chapter 11). After detection of labeled probes on a hybridization filter, it is a common practice to expose the hybridization filter to denaturing conditions such as solution of low ionic strength and high temperature, in order to wash the hybridizing probe molecules from the filter, making the filter ready for re-hybridization with a different hybridization probe (Protocols for DNA and RNA Transfer, DNA Electrotransfer, and Protein Transfer to Biodyne A Nylon Membranes, Pall Ultrafine Filtration Corporation, East Hills, N.Y., 1985, page 14).

Sets of oligonucleotides of defined sequence are used as primers for polymerases in polynucleotide synthesis and in nucleic acid amplification, for example, by the polymerase chain reaction (PCR, see Erlich, PCR Technology, Stockton Press, New York, 1989, in entirety). Sets of oligonucleotides of defined sequence are also used as probes of macromolecular structure, and are screened to identify oligomers which, either as antisense or as triplex-forming oligonucleotides, bind specifically to a native target nucleic acid such as a folded mRNA molecule (see, for example, Milner et al., Nature Biotechnology, 1987, Vol. 15, pages 537–41; and U.S. Pat. No. 5,176,996).

More recently, oligonucleotides have been immobilized or synthesized in micro-arrays on solid supports of material such as glass or $SiO_2$. "DNA chips" produced in this manner are useful for detecting or capturing multiple nucleic acid targets, for determining the nucleic type sequence of a target nucleic acid, for simultaneous analysis of the expression of thousands of genes, large scale gene discovery, DNA polymorphism screening, and mapping of genomic DNA clones, and are well suited for use in medical diagnostic assays for detection of pathogen infection and genetic mutation (for example, see U.S. Pat. No. 5,445,934; U.S. Pat. No. 5,503, 980; U.S. Pat. No. 5,605,662; Caviani-Pease et al., 1994, PNAS, Vol. 91, pages 5022–6; and reviews by Ramsay, 1998, Nature Biotechnology, Vol. 16, pages 40–44; and Marshall et al., 1998, Nature Biotechnology, Vol. 16, pages 27–31).

Fodor et al. (U.S. Pat. No. 5,445,934, col. 3–21, 23–32) describes photolithographic solid-phase synthesis of arrays of oligomers, including arrays of oligonucleotides of known nucleotide sequence. The oligomer arrays are synthesized on a substrate by attaching photo-removable groups to the surface of a substrate, exposing selected regions of the substrate to light to activate those regions, and attaching monomeric subunits with photo-removable groups to the activated regions. The steps of photo-activation and attachment can be repeated until oligomers of desired length and sequence are synthesized. According to the current state of the art pertaining to the photolithographic synthesis of polynucleotide arrays, there is only a 92–94% chance that a new nucleotide will be incorporated where desired (McGall et al., J. Am. Chem. Soc., 1997, vol. 119, pages 5081–90). Current technology thus imposes certain constraints on the possible array configuration, such as a practical upper limit on the number of nucleotides of approximately ten.

McGall et al. (U.S. Pat. No. 5,412,087, col. 4–20) describes substrates with surfaces to which are attached compounds having a thiol functional group protected by a photo-removable protecting group, which compounds can be used to construct arrays of immobilized anti-ligands, such as oligonucleotide probes.

Heller et al. describe a "master" DNA chip comprising a controllable, integrated array of micro-electrodes, and teaches denaturing double-stranded complexes comprising oligonucleotides at selected sites by increasing the negative potential and by use of chemical denaturants, in a process in which the oligomers hybridized at the selected sites are transferred to, or "printed" onto, another chip (U.S. Pat. No. 5,605,662, col. 20, lines 16–39).

DNA oligonucleotides of defined sequence can also be used as structural components of an electronic computer chip (Hollenberg et al., U.S. Pat. No. 5,561,071).

As is apparent from the preceding discussion there are numerous computational, data transmission-related, molecular biological, biochemical, and diagnostic applications which require the use of sets of oligonucleotides or oligonucleotide analogs of defined sequence and length. There currently is a need for a method for rapidly and efficiently providing the various combinations of oligomers required for applications such as those discussed above.

BRIEF SUMMARY OF THE INVENTION

Presented here is a rapid and efficient method for providing a selected set of oligonucleotides and/or oligonucleotide analogs comprising known subunit sequences. The method comprises the steps of a) obtaining a device for storing and providing oligomers comprising a substrate that supports an array of oligomer depots;

wherein each depot comprises a surface to which are attached a plurality of oligonucleotides and/or oligonucleotide analogs having a selected subunit sequence;

wherein the subunit sequence of the oligomers attached to at least one of said depots is different from the subunit sequence of the oligomers attached to a different depot of said array; and wherein oligonucleotides and/or oligonucleotide analogs comprising selected subunit sequences are stored at a plurality of depots of said array by being hybridized by Watson-Click pairing to the oligomers attached to the surfaces of said depots to form double-stranded complexes;

b) locally denaturing double-stranded complexes of at least one selected depot of the intact array to release oligomers stored therein, without effecting significant denaturation of double-stranded complexes of the unselected depots of the array; and c) collecting the oligomers released as a result of locally denaturing double-stranded complexes of said at least one selected depot.

The substrate that supports the array of oligomer-storing depots can be flexible, e.g., a nylon filter, or it can be of a rigid material such as $SiO_2$ in a DNA chip.

The array of depot sites may consist of from 2 to $10^7$ delimited areas wherein as many different types of oligomers are stored. The diameter of the area of each oligomer depot surface to which oligomers are attached can range from about 1 micron to 1 centimeter or more. Using known methods and currently available technology, one skilled in the art can readily fabricate an array of depot sites which are 5–10 microns in diameter, in which array the array density is about $10^6$ depot sites per $cm^2$.

Oligomers comprising a selected subunit sequence can be attached at a depot site directly to the area of substrate surface delimited by the depot boundaries, or they may be attached to the surface of a separate layer of material that is, in turn, attached to the substrate surface at the depot site.

Oligomers are attached to their respective depot sites using protocols known by those skilled in the art for attaching oligomers to a substrate so that the attached oligomers are able to hybridize efficiently with nucleic acids comprising a complementary nucleotide sequence.

The oligomers of known sequence attached to the array of depot sites can be synthesized by methods for synthesizing oligonucleotides and oligonucleotide analogs which are known to those skilled in the art. For example, they can be synthesized in situ on the supporting substrate, e.g. by photolithographic methods, or they can be pre-synthesized and deposited at the depot site, e.g. by micropipette, for chemical attachment.

The present invention also features a method wherein the oligomers of known subunit sequence that are attached to the array of depot sites are synthesized by a novel method which uses local melting of hybridized DNA, DNA ligase, and a restriction enzyme.

In all of the procedures involved in storing and releasing selected oligomers according to the present invention, the depot surfaces to which oligomers are attached are immersed in, or in contact with, buffered solutions of composition suitable for the biochemical or molecular biological operations being carried out.

Depot sites within the array are thermally insulated and/or physically separated from each other so that denaturation of double-stranded oligomer complexes at the selected depots does not cause denaturation of double-stranded complexes at the non-selected depots.

A collection of soluble oligomers of known composition is obtained by locally denaturing double-stranded complexes of the depots of the intact array comprising the desired oligomers, to yield the desired single-stranded oligomers in quantity related to the time and extent of the denaturing treatment. The oligomers are then collected in the buffer solution in which the array is immersed, for use in whatever application is contemplated.

A storage device comprising $10^6$ storage depot sites is able to store every possible oligomer 10-mer sequence ($4^{10}$ is approximately equal to $1.0 \times 10^6$). Using a storage device comprising about $10^6$ depot sites and storing every possible 10-mer, it is possible, with the present invention, to rapidly provide primers or hybridization probes that are complimentary to sites in any target nucleic acid. Also using such a storage device according to the present invention, a primer or hybridization probe of length greater than 10 subunits can be obtained rapidly by providing a set of oligomers of selected subunit sequence which, when ligated end-to-end, produce the desired longer polynucleotide.

Suitable applications for which oligomers can be provided according to the present invention include, but are not limited to, nucleic acid computation, nucleic acid amplification, polynucleotide synthesis by primer extension or by ligating oligonucleotides together end-to end, nucleic acid hybridization for detection or isolation of a target nucleic acid, and data encryption and transmission.

The present invention offers the advantages of rapidly and efficiently providing diverse, custom sets of oligomers, as needed, from a compact and easily accessed storage device. The invention is particularly advantageous for nucleic acid computation, and for encryption and transmission of data in the form of selected sets of hybridizing oligomers, since numerous sets of different oligomers having particular length and sequence properties are needed for both of these technologies, and these can be provided with facility by the present invention.

DETAILED DESCRIPTION OF THE INVENTION

Figure 1:
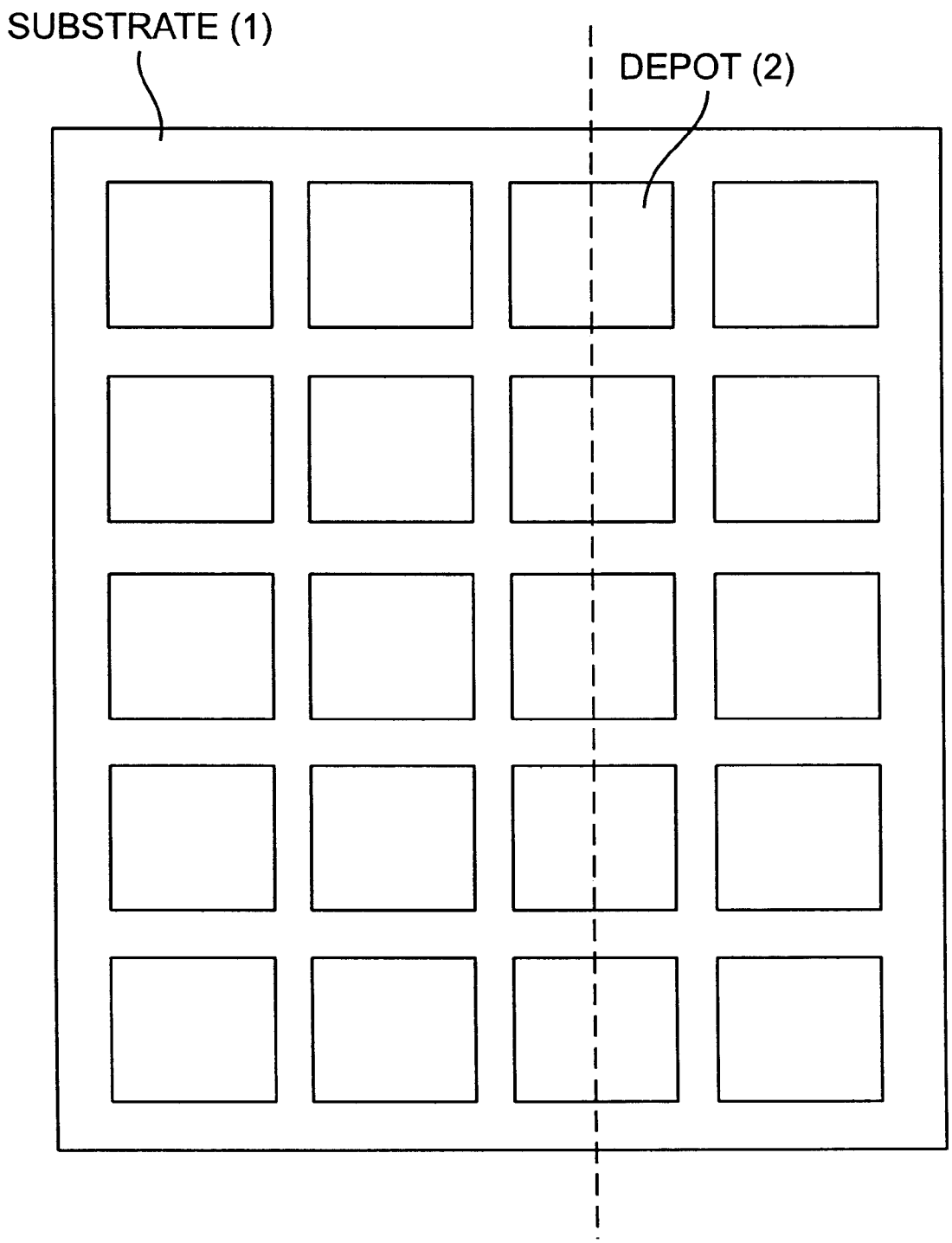
FIG. 1 schematically represents an oligomer-storing device comprising a substrate (1) supporting an array of oligomer depot sites (2). The dotted line indicates the section giving the view shown in FIG. 2.

This invention features methods wherein custom sets of oligonucleotides and/or oligonucleotide analogs having selected subunit sequences are rapidly and efficiently provided by their controlled release from depot sites of an oligomer storage device.

The practice of the present invention will employ, unless otherwise indicated, conventional techniques of chemistry, biochemistry, molecular biology, recombinant DNA, and medical diagnostic technology, which are within the capabilities of a person of ordinary skill in the art. Such techniques are explained in the literature. See, for example, Sambrook et al., 1989, Molecular Cloning: A Laboratory Manual, Second Edition, Books 1–3, Cold Spring Harbor Laboratory Press; B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, IRL Press; and, D. M. J. Lilley and J. E. Dahlberg, 1992, Methods of Enzymology: DNA Structure Part A: Synthesis and Physical Analysis of DNA Methods in Enzymology, Academic Press. Each of these general texts are herein incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Nucleic Acid Oligomers

The brief summary of DNA and RNA which follows is not meant to be exhaustive of the subject, but merely to provide a general framework for understanding the present invention. A more complete description of DNA and RNA technology is available in a number of texts, including: J. D. Wilson, M. Gilman, J. Witkowski, and M. Zoller, 1992, "Recombinant DNA", Second Edition, Scientific American Books; and, B. Lewin, 1997, "Genes VI", Oxford University Press. Each of these general texts are herein incorporated by reference.

As set forth above, the present invention relates to nucleic acid biochemistry and molecular biology. Genetic information is stored, transmitted, and expressed by nucleic acids, DNA and RNA, which are constructed of nucleotide subunits. In general, oligonucleotides are linear sequences of a few nucleotides (the Greek-derived prefix oligo-indicates "a few"), while linear sequences of many nucleotides are called polynucleotides (the Greek-derived prefix poly- indicates "many"). The choice of whether to refer to a nucleic acid of a given number of nucleotide subunits as a polynucleotide or as an oligonucleotide is arbitrary. Oligomers are linear sequences of relatively few subunits. A number followed by the suffix -mer refers to an oligomer of the indicated number of nucleotide subunits. For example, an oligomer that contains 12 or 17 bases is referred to as a 12-mer or as a 17-mer, respectively. Each nucleotide contains a phosphate group, a sugar moiety, and either a purine or pyrimidine base. The sugar of DNA is deoxyribose while the sugar of RNA is ribose. Nucleosides consist of a purine or pyrimidine base attached to ribose or deoxyribose. Polynucleotides and oligonucleotides each consist of a linear sequence of nucleotides of DNA or RNA in which the 3' position of the sugar of one nucleotide is linked through a phosphate group to the 5' position of the sugar on the adjacent nucleotide. Ligation is the formation of the phosphodiester bond which joins the adjacent nucleotides in the same nucleic acid chain. Two purine bases and two pyrimidine bases are found in both DNA and RNA. The purines adenine (A) and guanine (G) and the pyrimidine cytosine (C) occur in both DNA and RNA. However, thymine (T) only occurs in DNA and uracil (U) only occurs in RNA. The nucleotides of DNA are deoxyadenylic acid, thymidylic acid, deoxyguanilic acid, and deoxycytidylic acid, while the corresponding nucleotides of RNA are adenylic acid, uridylic acid, guanylic acid, and cytidylic acid. The sugar-phosphate backbones are on the outside of the DNA molecule and the purine and pyrimidine bases are on the inside, oriented in such a way that they can form hydrogen bonds to bases on opposing chains. Adenine (A) can pair only with thymine (T), while guanine (G) can bond only with cytosine (C). Hybridization is the process by which two complementary RNA and DNA strands pair to produce an RNA-DNA hybrid, or by which two complementary DNA single strands pair to produce a DNA—DNA hybrid, also known as double-stranded DNA. Universal base analogues or universal nucleotides are capable of hybridizing with any one of the four DNA nucleotides (Nichols et al., Nature, 1994, Vol. 369, pages 492–3; and Loakes et al., Nucleic Acids Research, 1994, Vol. 22, pages 4039–43). An example of a universal base analogue is 5-Nitroindole (Loakes et al., Nucleic Acids Research, 1994, vol. 22, pages 4039–43).

As used herein, the term oligomers refers to RNA or DNA oligonucleotides, RNA or DNA oligonucleotide analogs, or a combination of RNA and/or DNA oligonucleotides and RNA and/or DNA oligonucleotide analogs, which can be attached to the storage device depot sites, or which can be stored by being hybridized to oligomers attached to the depot sites.

Depending on the purposes for which the oligomers are to be used, the RNA or DNA oligonucleotide analogs can be oligomers in which from one to all nucleotide subunits are replaced with a nucleotide analog to confer desired properties such as detectability, increased hybridization affinity, resistance to degradation by nucleases, or the ability to covalently modify a target nucleic acid. Such oligonucleotide analogs include but are not limited to oligomers comprising 2'-O-alkyl ribonucleotides, phosphorothioate or methylphosphonate internucleotide linkages, peptide nucleic acid subunits (see U.S. Pat. No. 5,714,331, in entirety), and nucleotides modified by attachment of radioactive, or fluorescent groups, groups which intercalate, cross-link or cleave a nucleic acid, or groups which alter the electronegativity or hydrophobicity of the oligomers. Methods for making and using oligonucleotides and oligonucleotide analogs such as those listed above are well known to those skilled in the art of making and using sequence-specific hybridizing oligomers.

The sizes of the oligomers attached to the depot site surfaces, and of the oligomers stored at the depots, can range from about 4 subunits to 1000 or more subunits in length. The stored oligomers can be longer, shorter, or the same length as the attached oligomers. Oligomers having different lengths, and oligonucleotide analogs having different chemical structures and properties, can be stored in different depots of the same array. Those skilled in the art appreciate that oligomer hybridization specificity and affinity are determined, in part, by the length and chemical structure of the oligomer, and are able to select the structural parameters of the oligomers attached to, and stored in, the depots of the oligomer-storing device that are appropriate for their intended use. For example, the subunit sequences of the attached and stored oligomers can be selected so that they do not comprise self-complementary sequences that stabilize folding of said oligomers into hairpin structures which interfere with formation of inter-strand duplexes. Additionally, the subunit sequences of the attached and stored oligomers can be selected so that the melting temperatures (Tm) of the double-stranded complexes formed by hybridization of the complementary portions of the attached and stored oligomers at all of the depots of the array are within a selected range, e.g., in the range of a selected Tm plus or minus about 5 degrees C., for more efficient control of oligomer storage and release.

The Oligomer Storage Device

Figure 2:
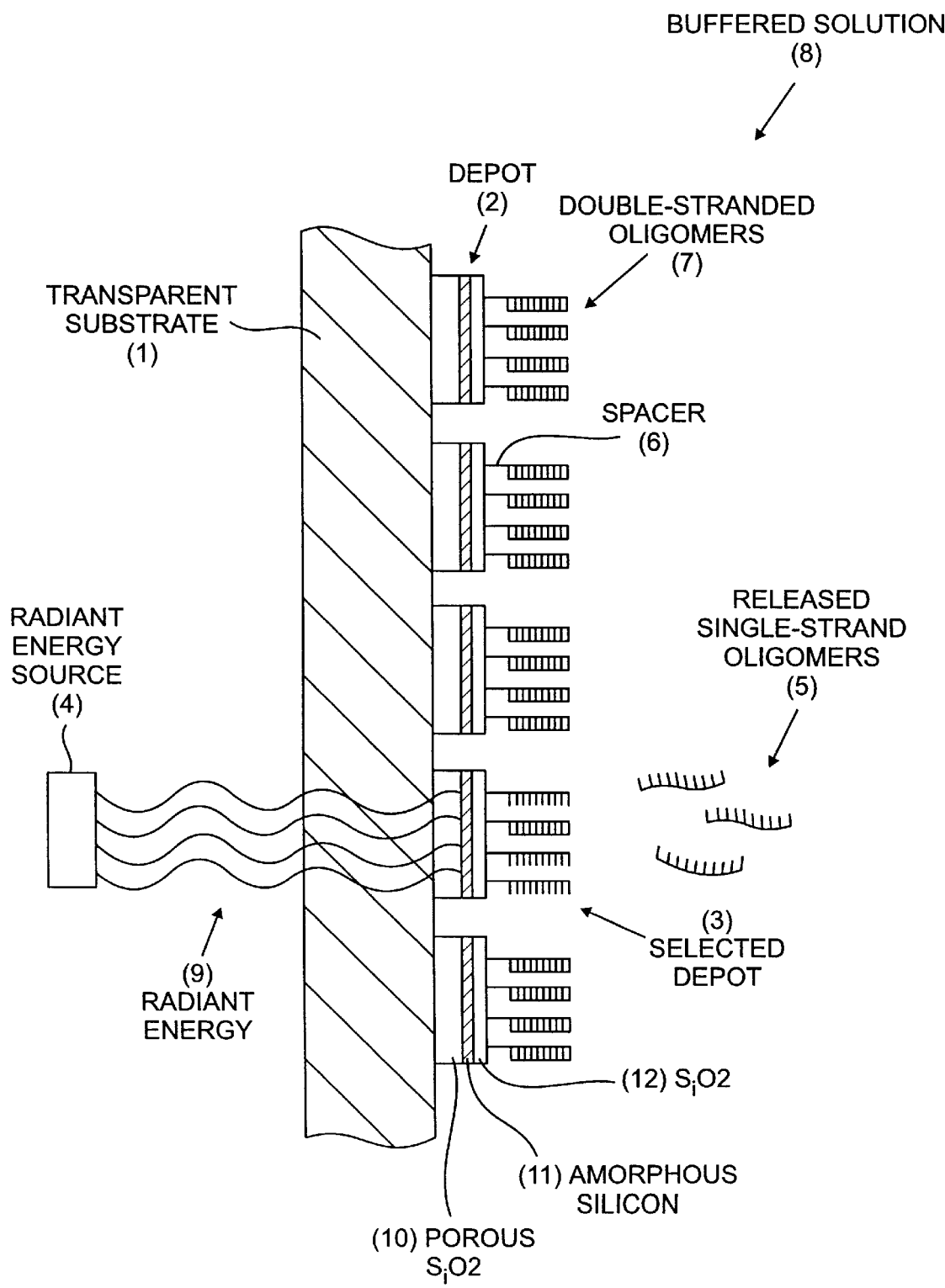
FIG. 2 schematically represents a cross-section through a row of depot sites of the oligomer-storing device shown in FIG. 1, for which the substrate (1) is a transparent substrate. A preferred embodiment of the present invention is shown wherein localized heating of a selected depot (3) is achieved by using a source of radiant energy (4) to irradiate the selected depot site through the transparent substrate (1) to release the desired single-stranded oligomers (5).

A central feature of the present invention is that the desired set of oligomers is provided from an oligomer storage device comprising a substrate (for example, see (1) in FIGS. 1 and 2) supporting an array of oligomer-storing sites, referred to herein as depots. The substrate can have a flat surface that supports the array, or it can be distributed in three dimensions, such as in a gel, a fibrous or granular matrix, or in a porous solid. By depot is meant a site at which oligomers are stored comprising a delimited area or volume that is part of or attached to the supporting substrate, to which are attached hybridizing oligomers comprising a selected subunit sequence (for example, see (2) in FIGS. 1 and 2). A depot site can have any size, shape, or volume, consistent with the objective of the invention of storing and selectively releasing oligomers as needed. By array is meant an arrangement of locations in or on the oligomer-storing device. The locations can be arranged in 2- or 3- dimensional arrays, or other matrix formats. FIG. 1 shows a 2-dimensional 4×5 array of depots on a supporting substrate. The number of locations in the array can range from 2 to $10^7$ or more. It is within the knowledge of those skilled in the art to fabricate a rigid substrate supporting an array of oligomer depot sites that can range in diameter from about 1 micron to 1 centimeter or more (see U.S. Pat. No. 5,412,087, col. 8, lines 50–68; U.S. Pat. No. 5,445,934, col. 9, lines 10–18; and Ramsay, Nature Biotechnology, vol. 16, p. 40, 1998). All of the depot sites of a given array can have the same diameter, or a single depot array can comprise depot sites having different diameters. The preferred method of the present invention features storing about $10^2$ to $10^7$ different types of oligomers of about 8 to 30 subunits in length in a micro-array of thermally isolated depot sites on a rigid substrate.

A substrate which is suitable for supporting immobilized nucleic acids for hybridization analysis can, in general, be adapted for use as an oligomer storage device of the present invention. Accordingly, a variety of different designs and materials are available for preparing the oligomer storage device of the present invention. For example, the storage device may be a flexible filter, e.g., of nylon or nitrocellulose, or it may be of a rigid material such as silica, silicon, glass, crystalline $Al_2O_3$ ("synthetic sapphire"), beryllium oxide, or a solid substrate coated with a noble metal such as gold. Methods for making such substrate supports for hybridizing oligomers are well known to those skilled in the art. (See U.S. Pat. No. 5,412,087, col. 6, lines 1–39; U.S. Pat. No. 5,445,934, col. 11, lines 49–63; Ramsay, Nature Biotechnology, vol. 16, pages 40–41; Drmanac et al., Genomics, 1989, vol. 4, pages 114–128; Mirkin et al., Nature, vol. 382, pages 607–609, 1996; R. Corn, DNA Computing Overview, last modified Mar. 13, 1998, <http://www.corninfo.chem.wisc.edu/writings/DNA overview.html>).

The oligomers attached at the depot sites can be attached directly to the surface of the substrate, or to the surface of a pad or pedestal-like structure that is in itself attached to the substrate, which pad or pedestal-like structure can be of material that is the same or different from that of the substrate. FIG. 2 shows oligomers attached to a depot site (2) comprising a pad comprising three different layers ((10), (11), and (12)) affixed to a rigid transparent substrate (1). The depot surface to which the oligomers are attached can be located on a raised feature or in a well-like depression on the surface of the supporting substrate.

Methods for making arrays comprising oligomers attached to depot sites to produce oligomer-storing devices for the present invention are well known. Such methods include in situ synthesis of oligomers attached at their 3' ends to a functionalized surface such glass, $SiO_2$, or GaAs (for example, see U.S. Pat. No. 5,445,934, col. 23, line 3, to col. 25, line 18; U.S. Pat. No. 5,412,087, col. 4, line 67 to col. 10, line 35; U.S. Pat. No. 5,605,662, col. 17, lines 21–63). Alternatively, pre-synthesized oligomers can be chemically attached to the substrate, e.g., by derivatizing the oligomers or the attachment surface, and then depositing microdroplets of the oligomers at the appropriate depot sites and allowing the oligomers to react with the depot site surface, or by attaching biotinylated oligomers to a streptavidin-coded surface (see U.S. Pat. No. 5,503,980, col. 13, lines 2–9; U.S. Pat. No. 5,412,087, col. 1, line 67 to col. 3, line 13 and col. 6, line 21 to col. 10, line 35; Marshall et al., Nature Biotechnology, vol. 16, pages 27–29, 1998; and Mirkin et al., Nature, vol. 382, pages 607–609, 1996).

A preferred mode of attachment of oligomers to depot surfaces for use according to the present invention is to use uncharged spacer groups ((6) in FIG. 2) to tether the oligomers to the depot surface (U.S. Pat. No. 5,445,934, col. 11, line 49, to col. 13, line 45; Caviani-Pease et al., P.N.A.S., 1994, vol. 91, pages 5022–24), as the use of such spacer groups is known to increase hybridization efficiency (Marshall et al., Nature Biotechnology, 1998, vol. 16, page 29).

Enzymatic Synthesis of Oligomers in situ

Figure 3:
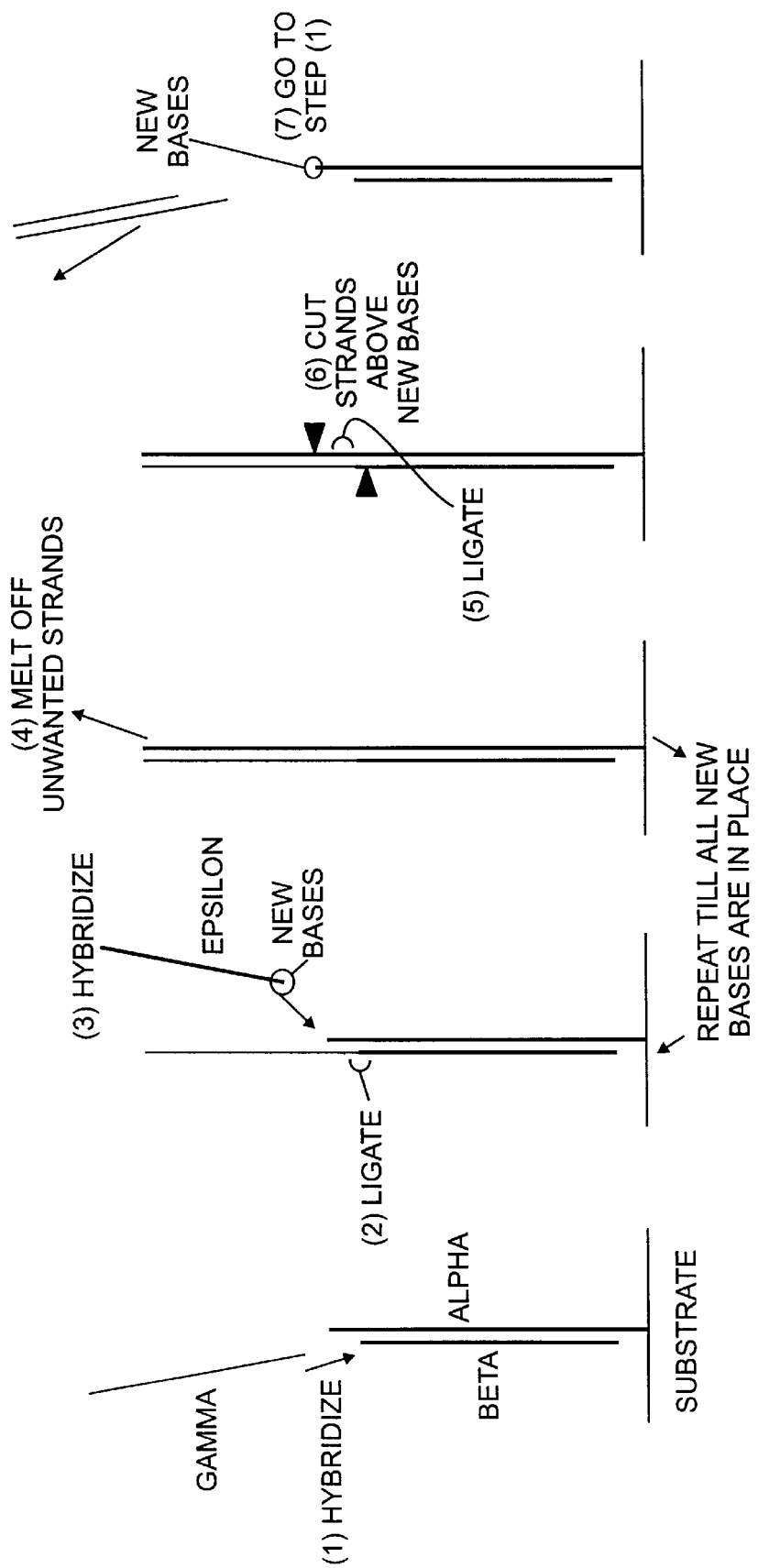
FIG. 3 schematically illustrates the seven basic steps of the disclosed ligation/restriction-based method for synthesizing an oligonucleotide array in which ε strands are hybridized to γ strands in step 3. The steps are described in detail below.
Figure 4:
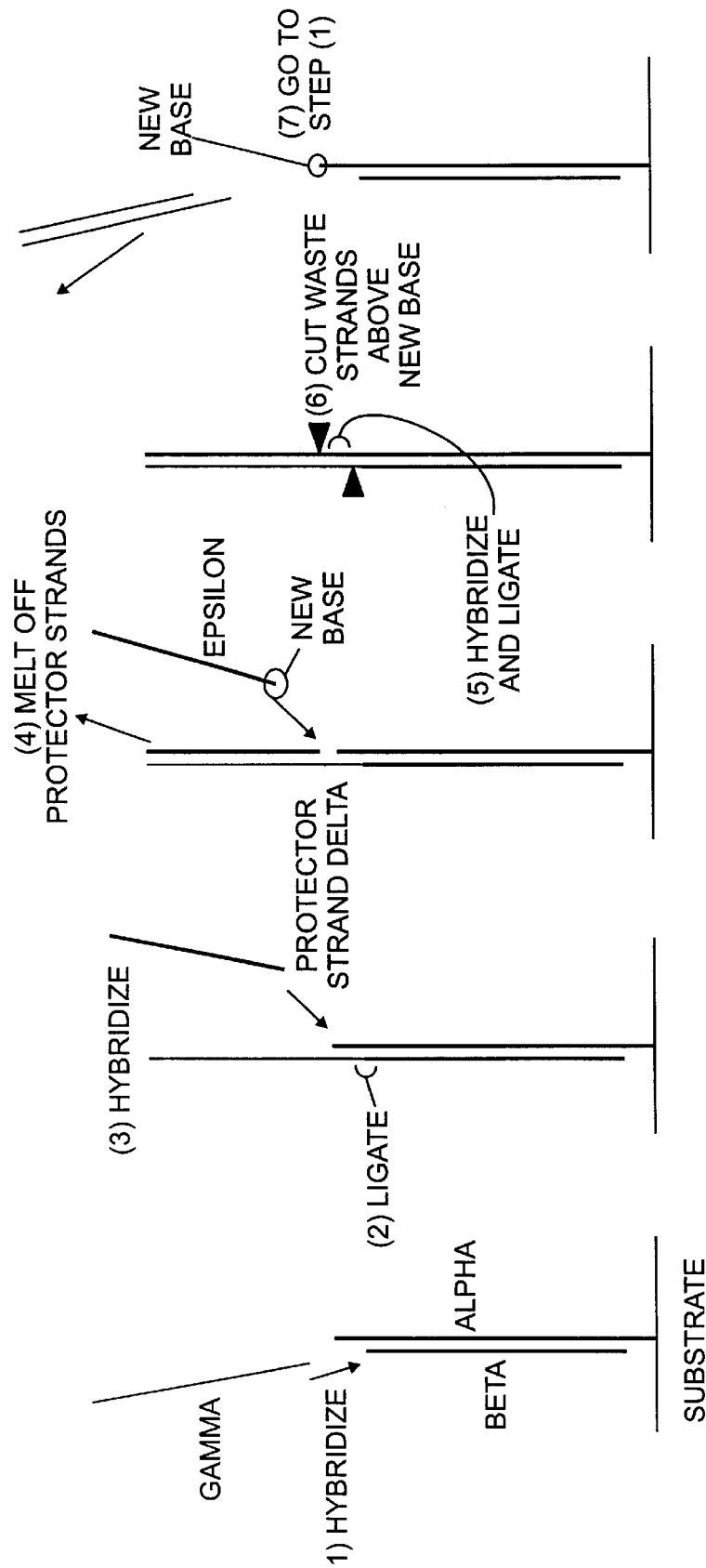
FIG. 4 schematically illustrates an alternative method for ligation/restriction-based synthesis of an oligomer array wherein protective δ strands are hybridized to the γ strands in those portions of the DNA-covered substrate where nucleotide addition is not desired.

An additional and novel method for making a substrate-supported array of oligomer depot sites which can be used as an oligomer-storing device for the present invention is described as follows. A double-stranded DNA consisting of an α strand and a complementary β strand, denoted α-β (alpha-beta), is synthesized by a known method of oligonucleotide synthesis (see M. J. Gait (Editor), 1984, Oligonucleotide Synthesis: A Practical Approach, IRL Press). One to four or more unpaired nucleotides at the phosphorylated 5' end of the α strand extend beyond the 3'-hydroxyl-terminated end of the complementary β strand as a single-stranded structure that is referred to as a "sticky end," because it can hybridize to another single-stranded nucleic acid having a complementary nucleotide sequence. The sticky 5' ends of the α strands are the sites where new nucleotides are added to the desired oligonucleotides being synthesized. Alternatively, the orientation of the strands of the duplex α-β oligomer with respect to the sticky end may be reversed, although suitable restriction enzymes needed in the nucleotide addition step discussed below are more rare in this case. New nucleotides may be added to the duplex α-β oligomers in a reaction in which the α-β oligomers are free in solution, or are attached to a substrate, as shown in FIGS. 3 and 4.

In one embodiment, a substrate is uniformly covered with duplex α-β oligomers, the DNA-covered surface is divided into local regions referred to as depots, and a different oligonucleotide sequence is synthesized in each depot. The duplex α-β DNA molecules are synthesized and attached to the substrate using known protocols; for example, α oligomers can be synthesized in situ on the substrate by a photolithographic method, and β oligomers can be synthesized by routine chemical methods and hybridized to the attached α oligomers; pre-fabricated α-β DNA molecules can be covalently attached to functionalized substrate SiO groups, biotinylated DNA oligomers can be bound to a streptavidin-coated surface, or thiolated DNA oligomers can be linked to a gold substrate, as discussed above. It is preferred that the 3' end of the α strand of the duplex α-β DNA oligomer be anchored to the substrate through an uncharged spacer group; however, the orientation of the strands of the duplex α-β oligomer with respect to the substrate may be reversed, although suitable restriction enzymes needed in step 6 below are more rare in this case, as noted above.

Synthesis of a different oligonucleotide sequence in each depot is achieved by a sequential series of hybridization, ligation, melting, and cleaving reaction, in which each depot is locally heated in turn so that ε (epsilon) DNA strands comprising the new nucleotides to be added hybridize only to DNA strands of the depot where addition is to occur. Localized heating of the DNA oligomers of the claimed invention may be achieved by any suitable means in accord with the types of oligonucleotides being synthesized, the type of substrate used, and the embodiment of the invention being employed. Suitable methods for locally heating depot sites are discussed in detail below. The temperature for heating is selected, with consideration to the lengths and sequences of the oligomers and to the ionic strength of the reaction solution, to rapidly melt off undesired DNA strands bound to the γ strands without melting the α-β duplex structures, so that the desired ε strands with the nucleotides to be added can hybridize to the exposed γ strands.

The synthesis of DNA strands according to the invention is illustrated as follows, referring to FIGS. 3 and 4 in embodiments in which the duplex α-β oligomers are attached to and uniformly cover a substrate. One possible substrate is comprised of a wafer of Si covered by (1) a thermally-insulating 1 μm thick layer of $SiO_2$, (2) a heat absorbing 0.5 μm thick layer of amorphous Si and (3) a 0.5 μm thick layer of $SiO_2$ upon which to anchor the DNA oligomers (see elements (10), (11), and (12), respectively, in FIG. 2). The substrate may be patterned into 10 μm×10 μm pads to better define and thermally isolate the identifiable areas (depots) of the plate. The α strand of the duplex α-β DNA oligomer is anchored to the substrate at its 3' end, and one to four or more unpaired nucleotides at its phosphorylated 5' end extend beyond the 3'-hydroxyl-terminated end of the complementary β strand to form a sticky end. In a preferred embodiment, the Si substrate is replaced with a substrate of transparent crystalline $Al_2O_3$ to allow back illumination of the desired depots, thus protecting the DNA from direct exposure to the laser radiation. Steps of hybridization, ligation, heating to melt desired portions of the duplex DNA complexes, and cleavage by restriction enzyme, are carried out in suitable buffered solutions for these reactions which are well known to those skilled in the art (see Sambrook et al. and the other previously cited references teaching biochemical and molecular biological methodology). In embodiments in which DNA molecules are synthesized on a substrate, the DNA-covered substrate is immersed in suitable buffer during each reaction step of the method.

Step (1): A set of single-stranded γ (gamma) DNA oligomers is prepared having phosphorylated 5' ends, and in which the nucleotide sequences at the 5' ends are randomly varied so that individual members of the set of γ strands can hybridize with every possible α strand sticky end. The set of γ oligomers is allowed to hybridize with the 5' sticky ends of the α strands. The bases of a number p of nucleotides in each γ strand adjacent to the randomized 5'-terminal nucleotides are universal bases, where p is the number of new nucleotides to be transferred from the ε strands to the ends of the α strands. In theory, p can range in value from 1 to as large a number as desired. In using the invention to make a set of long oligonucleotides which differ from each other at only one or a few nucleotides, it may be practical to use oligomers having large p, so as to add large blocks of nucleotides to the ends of the α strands in a single step. In using the invention to make an array of highly variable oligonucleotides, the upper value of p is limited by the practical need to repeat the steps for adding p nucleotides up to $4^p$ different times for each set of p nucleotides that are added.

Step (2): In the presence of T4 DNA ligase and ATP, the 5' ends of the γ strands become ligated to the 3' ends of the β strands.

Step (3): Desired strands ε (epsilon) are introduced to hybridize to the γ strands, wherein the ε strands have p nucleotides at their 3' ends which are to be added to the α strands. Since there are $4^p$ different types of ε strands, p being the number of bases added in each step, with each different ε strand ending in one of the $4^p$ possible sets of p bases, this step would need to be repeated once for each of the different p-tuples of bases added to the entire substrate or plate, prior to ligating. The ε strands hybridize with the γ strands, with the p bases to be added pairing with the p universal bases on the γ strands. The overall lengths and nucleotide sequences of the γ and ε oligomers are selected so that γ and unligated ε strands form a duplex structure that melts at a temperature at which the α-β duplexes remain intact. A preferred configuration for the α-β-γ-ε complex is one wherein the 5' ends of ε strands and 3' ends of γ strands form blunt ends.

Step (4): In the case where a single type of oligonucleotide is being made, nicks between the 3' hydroxyl terminations of the ε strands and the 5' phosphate terminations of the α strands are ligated according to Step 5 below.

In the case where an array of different substrate-bound oligonucleotides is being synthesized, with new nucleotides also being added to the ends of DNA oligonucleotides at other locations on the substrate, the undesired ε strands are removed by local heating without melting the α-β duplex portions, for example, by using laser illumination patterned with a lithographic mask, and are washed away. Desired ε strands are then hybridized to exposed γ strands of substrate-bound DNA molecules at the heated locations, by repeating Step 3. Steps 4 and 3 of heating to selectively remove undesired ε strands, and then hybridizing desired ε strands at each location where nucleotides are to be added, are repeated until all locations where nucleotides to be added to the sticky ends of the substrate-bound DNA have been treated.

Step (5): After all desired ε strands are hybridized to the growing DNA molecules, nicks between the 3' hydroxyl terminations of the ε strands and the 5' phosphate terminations of the α strands are ligated using T4 DNA ligase again.

Step (6): The resulting double-stranded DNA molecules are cut with a restriction enzyme that leaves a new sticky end similar to the original α-β sticky end, except that cleavage results in addition of p new nucleotides to the 5' end of the α strand. Cleavage may also result in addition of one or more paired nucleotides to the 3' end of the β strand. In the preferred method, the restriction enzyme that is used is one that cuts at a site adjacent to, but outside of, its specific recognition sequence that is built into the ε-γ sequence, to leave the new sticky end on the growing double-stranded oligonucleotide. An example of such a restriction enzyme which is suitable for use in the invention is Alw 26 I. Restriction enzyme recognition sites in the growing α-β duplex can be protected from unwanted cleavage by methylation of one or both strands at the enzyme recognition site in the α-β duplex to be protected, using the appropriate methylase enzymes, or by incorporation of a methylated nucleotide or a restriction-enzyme-inhibiting nucleotide analog, which incorporation could be carried out during synthesis of the original α-β duplex stem, or in the step wherein new bases are added to the growing duplex DNA molecule.

Step (7): The process is repeated for each new set of bases to be added to the growing duplex DNA molecules.

One skilled in the art can readily design the original α and β oligomers to comprise a recognition site for a restriction enzyme that is different from the one used in the synthetic reactions, so that the polymers can be released after synthesis, if desired.

An alternate and less-preferred procedure is illustrated in FIG. 4 in which steps 3–5 are modified to include use of protective δ strands as follows:

Step (3, modified): An excess of δ (delta) protector strands are prepared which are perfectly complementary to all of the nucleotides of the single-stranded portion of the γ strands extending from the α-β duplex, except that the δ strands comprise 3'-phosphate-terminated ends, or they lack a complementary nucleotide at their 3' ends, so that unwanted ligation of the 3' ends of the δ strands to the 5'-ends of the α strands is prevented. The excess of δ protector strands are introduced to hybridize to and protect the γ strands in non-reacting depots from binding to nucleotide-adding ε strands.

Step (4, modified): In desired locations, the protector δ strands are melted off the γ strands by local heating, for example, by using laser illumination patterned with a lithographic mask, and are washed away. Desired strands ε (epsilon) are then introduced to hybridize to the single-stranded γ oligomers. The remaining steps of the alternate method are as described above for the method in which protector δ strands are not used. If one wants to make some of the strands shorter than normal, so that the δ strands need to be left in place during the restriction step, the strands containing a δ may be protected from cutting by methylation of the restriction enzyme recognition site on the δ strand.

The fidelity of synthesis attained using the above-described method for oligomer synthesis of the present invention permits efficient and accurate synthesis of oligonucleotides in substrate-bound arrays that are considerably longer than those that can be accurately made using current technologies; for example, substrate-bound oligonucleotides of up to 20, 30, 50, or even 100 or more nucleotide subunits, can be accurately made by the present invention.

Storing Oligomers in Depots

Oligomers are stored in the depot array of the storage device by allowing them to hybridize specifically to oligomers comprising complementary subunit sequences which are attached at the depot sites ((2) in FIG. 2), to form double-stranded oligomer complexes attached to the depot sites ((7) in FIG. 2). Those skilled in the art recognize that the number of consecutive complementary nucleotides that must be present in an oligonucleotide so that it hybridizes specifically to a target nucleic acid molecule can vary considerably, from about 4 up to 14 or more, depending on such factors as the complexity of the set of target nucleic acids and the physical conditions (ionic strength, temperature, anionic and cationic reagents, etc.) used in the hybridization and wash steps. The statement that a soluble oligomer hybridizes specifically to a substrate-bound oligomer or other target nucleic acid is intended to mean that a portion of the oligomer comprising a nucleotide sequence complementary to a sequence in the substrate-bound oligomer or other target nucleic acid binds by Watson-Crick base-pairing to the complementary portion of the substrate-bound oligomer or other target nucleic acid to form a stable double-stranded complex, under hybridization conditions that are sufficiently stringent that oligomer molecules having fewer bases complementary to, or forming less stable duplex structures with, said substrate-bound oligomers or other target nucleic acids do not hybridize to said substrate-bound oligomers or other target nucleic acids and form stable double-stranded complexes. Selection of parameters such as the lengths of the complementary portions of the soluble and substrate-bound oligomers and the conditions used in hybridization and wash steps, so that the soluble oligomers hybridize specifically to their substrate-bound counterparts, is well within the capabilities of a person of ordinary skill in the art (e.g., see Sambrook et al., 1989, supra, Chapter 11).

For example, a complete set of oligonucleotides comprising every possible sequence of n consecutive nucleotide subunits can be stored in an array of $4^n$ depot sites comprising complementary oligomers by exposing the array to the soluble oligomers at a temperature about 25° C. below the lowest melting temperature for the set of double-stranded complexes to be formed, in a suitable buffer containing a high molar concentration of $Na^+$. The time required to saturate the $4^n$ depot sizes with the n-mer oligomers is known to be dependent on the concentrations of the oligomers, the temperature, and the concentration of $Na^r$ ions. If the soluble oligonucleotides are applied at a concentration of 0.5 mole of single nucleotides per liter and the $Na^+$ concentration is 1 mole per liter, the time for half of the hybridization reaction to be completed is about 4 seconds for n=10, and about 100 days for n=20. (Britten et al., Methods in Enzymology, 1974, vol. 29, part E, pages 363–418; Wetmur et al., J. Molecular Biology, 1989, vol. 31, page 349; Britten et al., Science, 1968, vol. 161, page 529).

Releasing Selected Oligomers

A custom set of soluble oligomers of known composition is obtained by locally denaturing double-stranded complexes of selected depots of the intact array comprising the desired oligomers, and collecting the oligomers released from the selected depots ((5) in FIG. 2) into the buffer solution in which the array is immersed ((8) in FIG. 2). Denaturation of oligomer complexes at selected depots can be achieved by any of the nucleic acid-denaturing treatments known to those skilled in the art of nucleic acid biochemistry. Those skilled in the art appreciate that the melting temperature of a double-stranded oligonucleotide complex is dependent on the length, nucleotide sequence, and chemical structure of the complex, and on the ionic strength and chemical composition of the solvent (see Sambrook et al., 1989, supra, page 11.46).

The preferred method for denaturing double-stranded complexes at the selected depots to release the desired oligomers is by locally heating the selected depots so as to subject the selected depots to a raised temperature under appropriate solution conditions for a period of time sufficient to release the desired oligomers from the selected depots. Localized heating of the selected depot surfaces can be achieved by any suitable means in accord with the structure and size of the supporting substrate, and the size and disposition of the individual depot sites. For example, selected depots can be locally heated by illuminating the surface of the array, in a suitable buffer and at a temperature below the melting point of the oligomer duplexes, with a pattern of focused irradiation from a radiant energy source ((4) and (9) in FIG. 2), e.g. an argon laser, that heats only those depots storing the desired oligomers. The laser can be mounted on a support which provides precise x-y translation control, to permit controlled heating of one depot at a time, in serial fashion. Alternatively, the laser can have a broad beam that can irradiate a mask, the image of which can irradiate all of the depots in the array at once. The mask can thus be used to shield the unselected depots so that only those comprising the desired oligomers are heated. To heat a single depot having a surface area of about 100 $\mu m^2$ to about 70° C. in a suitable buffered solution to locally melt double-stranded DNA duplexes stored at the heated depot will require roughly 10 milliwatts of argon laser light (488 nm). Use of a substrate which is transparent to argon laser light, e.g. crystalline $Al_2O_3$, to support thermally isolated, light-absorbing, depot surfaces to which the oligomers are attached, allows back illumination of the desired depots as shown in FIG. 2, thus protecting the oligomers from direct exposure to the laser radiation. A substrate of $Al_2O_3$ is also advantageous because the high thermal conductivity of $Al_2O_3$ permits the substrate to act efficiently as a heat sink, by drawing heat away from the irradiated depot sites and so providing greater thermal isolation of the unselected depot sites. Alternatively, the storage device substrate comprising the depot array could be in contact with, or have integrated within it, a controllable, addressable, array of resistive heating elements which is spatially aligned with the depot array, so that application of current to selected resistive heating elements locally heats selected depots proximal to the activated heating elements to release the desired oligomers. Heller et al. teach fabrication of a silicon substrate into which is integrated a micro-array of electronically addressable micro-locations corresponding to a micro-array of DNA storage sites (U.S. Pat. No. 5,605,662, col. 9–10, 12–16). Accordingly, it is within the knowledge of those skilled in the art of microlithography and thick film circuitry to fabricate a DNA chip in which there is integrated an array of electronically addressable micro-locations comprising resistive heating elements such as can be formed, for example, by depositing undoped polycrystalline silicon at positions between addressable conducting wire grids (Kamins, Polycrystalline Silicon for Integrated Circuit Applications, 1988, Kluwer Academic Publications, Boston). As described by Heller et al., metal contact pads along the outside perimeter of the chip permit wiring such a chip comprising an integrated electronically addressable micro-array to a microprocessor-controlled power supply and interface for controlling the device (U.S. Pat. No. 5,605,662, col. 12). The amounts of oligomers released by localized heating can be controlled by varying the amount of heat applied, e.g., by controlling the intensity of the laser light or the temperature of the resistive heater, and/or by varying the time period during which heat is applied. According to the preferred method, the localized heating of selected depots to release desired oligomers stored therein is electrically controlled by a programmable microprocessor and an interface for controlling the process. By the method of the present invention, local heating of selected depots will cause oligomer duplexes at the heated depots to melt in a short time of the order of seconds, to yield single-stranded oligomers in quantities related to the time and extent of heating.

Heller et al. teach that denaturation of DNA at selected depots can also be induced by locally increasing the negative electric potential at the selected depots (Heller et al., U.S. Pat. 5,605,662, column 20). Thus, an array of microelectrodes integrated within, or closely associated with, a substrate supporting an oligomer-storing array of depot sites can be used to create denaturing conditions at selected depots of the array to practice the present invention. In addition positively charged chaotropic agents and other denaturants can be added to the solution in contact with the selected depots to promote denaturation of the attached double-stranded complexes. Exposure to denaturing solution conditions can be limited to the depots selected for denaturation by surrounding the selected depot surfaces with a liquid-impermeable barrier that prevents the denaturing solution from contacting non-selected depot surfaces. For example, individual depots of a large-scale array, in which depot surfaces are 0.1 to 10 mm or more in diameter, can be situated in wells or surrounded by raised divider walls to be "fluidically isolated" from each other, so that selected depot surfaces can be exposed to denaturing solution without also exposing non-selected depot surfaces to the denaturing conditions. Denaturation of selected depots, whether by localized heating, application of increased negative potential, denaturing solution, or any combination of these means, can be carried out serially, one depot at a time, or in parallel with multiple depots being treated simultaneously.

Collecting and Using the Released Oligomers

Oligomers released from selected depot sites following denaturation of double-stranded complexes at those sites ((5) in FIG. 2) are collecting by collecting the solution in contact with the treated depot surfaces ((8) in FIG. 2). The solution in contact with the oligomer-storing depot array can be enclosed or contained within a reservoir, and once the desired oligomers are released into the solution, it can be collected by any suitable means, e.g. by a manually operated or automated pipetting device, or a syringe. Alternatively, the solution containing the desired oligomers can be removed from the reservoir and transferred to a suitable collecting device, and fresh solution can be added to the reservoir in its place, e.g. to wash away residual oligomers in preparation for releasing a different set of oligomers, by using automated or microprocessor-controlled pumps which direct the flow of the different solutions through tubes connected to the reservoir.

The collected oligomers may then be used in protocols which employ a customized set of oligonucleotides or oligonucleotide analogs. Such protocols include, but are not limited to, protocols for nucleic acid computation, nucleic acid amplification, polynucleotide synthesis by primer extension or by ligating together overlapping complimentary oligonucleotides, nucleic acid hybridization for detection or isolation of a target nucleic acid, and data encryption and transmission.

EXAMPLES

The following examples further demonstrate several preferred embodiments of this invention and are offered by way of illustration, but should not be construed as limiting the claims thereof. Those skilled in the art will recognize numerous equivalents to the specific embodiments described herein. Such equivalents are intended to be within the scope of the claims.

Example 1
Synthesis of a DNA oligonucleotide by the ligation/restriction method

As a concrete example for the case in which a single base is to be added to the strands in each step (i.e., p=1), the following oligomers are selected to carry out the needed reactions:

34-mer, α: 5' TCTTAACATAGGAATTTGAGGCAG-TACGCAAAAA 3'-biotin (B) (SEQ ID NO: 1).

30-mer, β': 3' AGAATTGTATCCTTAAACTCCGTCAT-GCGT 5' (SEQ ID NO: 2).

26-mer, β: 3' TTGTATCCTTAAACTCCGTCATGCGT 5' (SEQ ID NO: 3).

17-mer, γ: 3' TCACGTCAGAGCNNNNN 5' (SEQ ID NO: 4), wherein the first N in the 3'→5' direction is a universal base and the subsequent N's designate A, C, G, or T.

13-mer, $\epsilon_A$: 5' AGTGCAGTCTCGA 3' (SEQ ID NO: 5).
13-mer, $\epsilon_T$: 5' AGTGCAGTCTCGT 3' (SEQ ID NO: 6).
13-mer, $\epsilon_G$: 5' AGTGCAGTCTCGG 3' (SEQ ID NO: 7).
13-mer, $\epsilon_C$: 5' AGTGCAGTCTCGC 3' (SEQ ID NO: 8).

The sequence of oligomer SEQ ID NO: 2 (β') consists of 18 A-T's and 12 G-C's, chosen to minimize the number of A-T and/or G-C matches of the sequence with itself for shifts of up to ±20 bases. It is further chosen to have no more than 3 A's, T's, or G-C's in a row; no more than 2 G's or 2 C's in a row. These selections are to ensure that the strands will not form hairpins. Oligomer SEQ ID NO: 2 (β') is chosen to lack the restriction enzyme Alw 26 I recognition sequence GTCTC/CAGAG or either of the four base pair segments of that sequence. Oligomer SEQ ID NO: 1 (α) is complementary to the full sequence of β', and has in addition a quartet of A's and a biotin group at the 3' end for attaching the α's to the substrate. SEQ ID NO: 3 (β) is identical to β' except that four bases are missing from the 3' end to produce a 4-base sticky end when hybridized to α. In oligomer SEQ ID NO: 4 (γ), the first N in the 3'→5' direction is a universal base, such as 5-Nitroindole, and each of the subsequent N's are random deoxyribonucleotide bases. The concentration of any one particular version of γ will be 1/256 of the total. The ε oligomers (SEQ ID NOs:5–8) each contain one of the two single-stranded sequences from the duplex DNA Alw 26 I restriction enzyme recognition sequence, which cuts leaving the 5' sticky end indicated:

5' . . . NNNGTCTCN 3' (SEQ ID NO: 9, from the ε strand)
3' . . . NNNCAGAGNNNNN 5' (SEQ ID NO: 10, from the γ strand), wherein the $5^{th}$ N from the 5' end of the γ strand is a universal base, and the other Ns designate A, C, G, or T.

The detailed steps in making a DNA hybridization array are as follows.

Step (1). We start by attaching α oligomers uniformly over the substrate, e.g., by using the affinity of biotin for a streptavidin-coated glass surface, and β strands are then hybridized with the anchored a strands, giving:

5' TCTTAACATAGGAATTTGAGGCAGTACG-CAAAAA 3'-B (α, SEQ ID NO:1)
3' TTGTATCCTTAAACTCCGTCATGCGT 5' (β, SEQ ID NO:3).

Step (2). The set of γ DNA strands (SEQ ID NO: 4) is introduced to hybridize with the sticky ends of the α strands, and the ends of the γ DNA strands are ligated to the ends of the β strands of the anchored α-β DNA by incubating with T4 DNA ligase and ATP, giving:

5' TCTTAACATAGGAATTTGAGGCAGTACG-CAAAAA 3'-B (α)
3' TCACGTCAGAGCNNNNNTTGTATCCT-TAAACTCCGTCATGCGT 5' (γ+β)

where the α strand is SEQ ID NO: 1, and the γ+β strand is SEQ ID NO: 11 wherein the first N in the 3'43 5' direction in γ is a universal base and the subsequent N's designate A, C, G, or T.

Step (3). The DNA-covered substrate is incubated in the presence of an oligomer denoted $\epsilon_X$ containing the base X to be added to the α strand, so that the $\epsilon_X$ oligomers hybridize to the γ strands. In this example, $\epsilon_A$=SEQ ID NO: 5; $\epsilon_T$=SEQ ID NO: 6; $\epsilon_G$=SEQ ID NO: 7; and $\epsilon_C$=SEQ ID NO: 8.

Step (4): To add one of the 4 bases A, T, G, or C, to DNAs of 4 or more different depots, the hybridization step would need to be repeated with each of the 4 different $\epsilon_X$ strands at the desired substrate locations prior to ligating and cleaving. After the first step in which an $\epsilon_X$ strand is hybridized to the substrate-bound DNA, and before each subsequent $\epsilon_X$ addition step, undesired $\epsilon_X$ strands are melted away from the DNA of the depots where the nucleotides are to be added by local heating, e.g., by using laser illumination patterned with a lithographic mask for 10 seconds to give a local temperature of approximately 70° C., thereby producing the same duplex DNA structure comprising a duplex α-β portion produced in Step 2, wherein γ DNA strands in the selected areas are receptive to one of the $\epsilon_X$ oligomers. Desired $\epsilon_X$ strands are then hybridized to exposed γ strands of substrate-bound DNA molecules at the heated locations by repeating Step 3. Local heating to selectively remove undesired $\epsilon_X$ strands without melting duplex α-β portions (Step 4), and hybridization of desired $\epsilon_X$ strands at each location where nucleotides are to be added (Step 3), are repeated until all depots where nucleotides are to be added have been treated with a desired $\epsilon_X$ oligomer.

Step (5): After all desired $\epsilon$ strands are hybridized to the growing DNA molecules, nicks between the 3' hydroxyl terminations of the $\epsilon$ strands and the 5' phosphate terminations of the $\alpha$ strands are ligated using T4 DNA ligase again. Ligation of the hybridized $\epsilon_X$ strands to the $\alpha$ strands by incubating with T4 DNA ligase and ATP gives:

5' AGTGCAGTCTCGNTCTTAACATAG-GAATTTGAGGCAGTACGCAAAAA 3'-B($\epsilon$+$\alpha$)

3' TCACGTCAGAGCNNNNNTTGTATCCT-TAAACTCCGTCATGCGT 5' ($\gamma$+$\beta$), where the $\gamma$+$\beta$ strand is SEQ ID NO: 11 as described above, and wherein and the $\epsilon$+$\alpha$ strand is SEQ ID NO: 12 wherein N is A, C, G, or T.

Step (6): The DNA-covered substrate is incubated at 37° C. with Alw 26 I restriction enzyme, and a small sticky-ended double-stranded oligomer is cut off and washed away producing:

5' NTCTTAACATAGGAATTTGAGGCAG-TACGCAAAAA 3'-B ($\alpha$+N)

3' NTTGTATCCTTAAACTCCGTCATGCGT 5' ($\beta$+N), where $\alpha$+N is SEQ ID NO: 13 and $\beta$+N is SEQ ID NO:14, wherein N is A, C, G, or T, and

5' AGTGCAGTCTCG 3' (SEQ ID NO: 15)

3' TCACGTCAGAGCNNNN 5' (SEQ ID NO: 16), wherein the first N in the 3'→5' direction is a universal base and the subsequent N's designate A, C, G, or T. This leaves the new deoxyribonucleotides X of $\epsilon_X$ added to the $\alpha$ strands, and the $\alpha$-$\beta$ strands in a state precisely like that encountered in step 2, except for being one base pair longer.

Step (7): The synthetic cycle is now repeated by returning to Step 2 of the above-described example. By repeating Steps 2–6 one may now add as many bases as desired in what ever pattern is needed.

Step (8): When the $\alpha$ strands have the desired sequence, the lengthened $\beta$ strands are melted off and washed away. The $\beta$' strands are then allowed to hybridize with the $\alpha$ strands, leaving the newly synthesized oligonucleotides in single-strand form, attached at their 3' ends to the blunt-ended $\alpha$-$\beta$ duplexes at the 5' ends of the $\alpha$ strands. If the number of added nucleotides happens to be four, this last step is not needed.

The $\epsilon$ strands are more than 50% G-C's and would be expected to dissociate at a rate of less than $10^{-4}$ s$^{-1}$ or less at 22° C., compared to $10^2$ s$^{-1}$ at 70° C. (from extrapolation of the data in FIG. 6 of Morrison et al., Biochemistry, 1993, vol. 32, pages 3095–3014; see also C. Cantor and P. Schimmel, Biophysical Chemistry, 1980, Freeman Press, New York, page 1217). The melting point for similar 14-mers is about 40° C. (Wallace et al., Nucleic Acid Research, 1979, vol. 6, pages 3543–3557). Thus, a 10 sec heat pulse raising the temperature of a spot to 70° C. will result in a 99.9% chance that a new base is incorporated where it is wanted and a similar chance that it is not incorporated elsewhere if the temperature there is less than 20° C. The $\beta$' strands dissociate at a rate of roughly $10^{-5}$ s$^{-1}$ at 70° C., and thus the structure should be quite stable under the temperature cycling needed for Steps 2–7.

It is estimated that when one depot is heated to the 70° C. required in Step 4 the temperatures of any unilluminated neighboring depots will not rise above 20° C. if the substrate is heat-sunk to near 0° C. Although the dissociation rates for oligomers are a steep function of temperature, the borders of the depots will contain sequences that do not correspond to the programmed growth. In operation, the area between the depots should not be subjected to heating; e.g., through use of a mask.

At concentrations of $10^{-6}$ M (moles per liter), hybridization reactions rates are of the order of 1 s$^{-1}$. The rate limiting steps in this scheme are the two ligation steps and the one restriction step. According to their catalog, one New England Biolabs (NEB) unit for the T4 DNA ligase gives 50% ligation of Hind III fragments in 30 m at a 5' DNA termini concentration of $10^{-7}$ M. Using a high concentration of enzyme will result in sufficiently complete ligation in a few minutes. The restriction enzyme will also act in a few minutes. The ligation and restriction enzyme cleavage steps need to occur only once in the four cycles. One may thus estimate that growth of a DNA array by the method described would take less than 30 minutes per four bases added, comparable to the 1 hour per four bases in the early light-directed synthesis work of Ref. 7.

Example 2

Figure 5A:
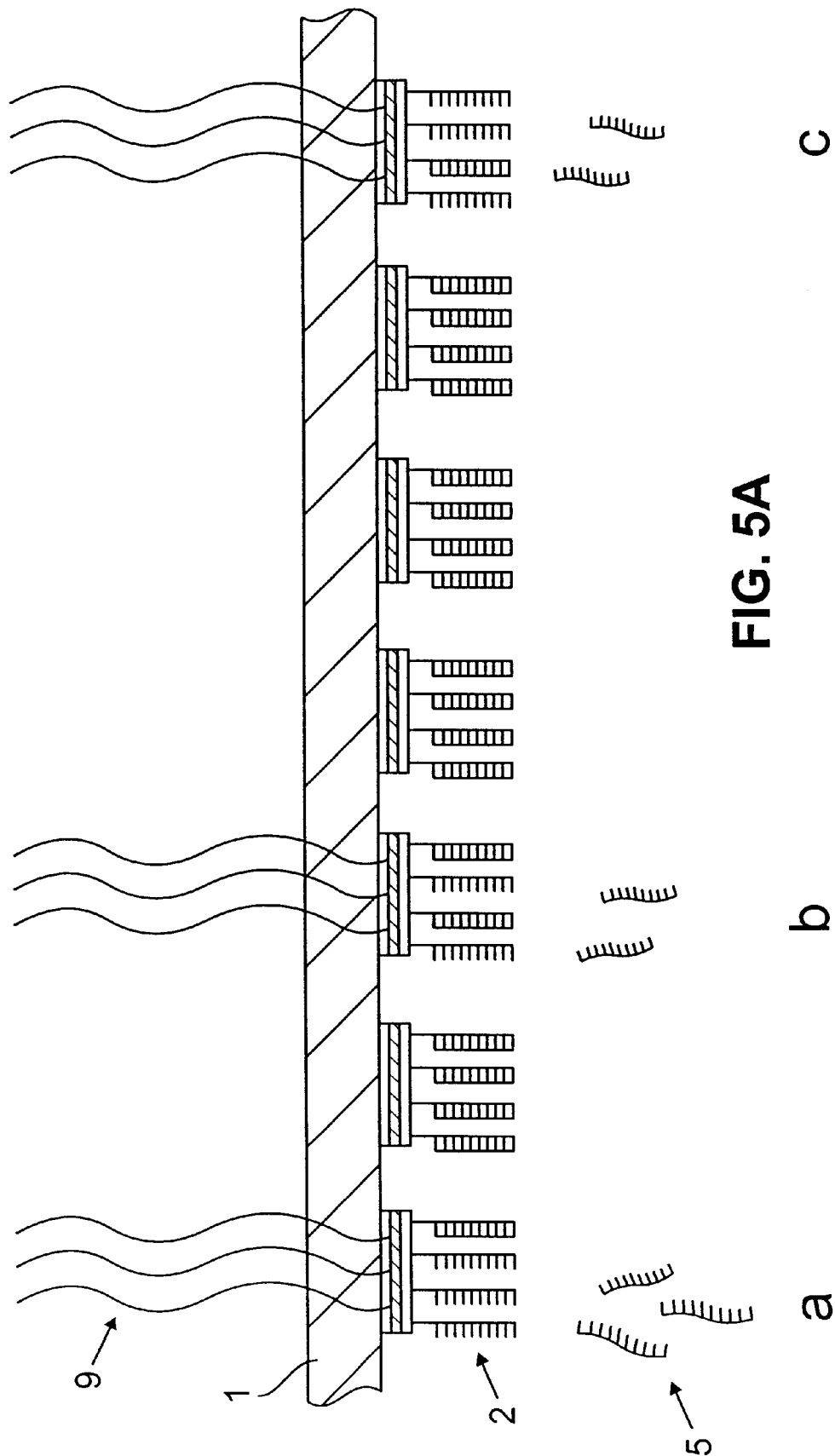
FIGS. 5A and 5B schematically illustrate a method in which selected DNA oligonucleotides are released from an oligomer storage device (FIG. 5A), and are ligated together to make a longer DNA molecule (FIG. 5B).
Figure 5B:
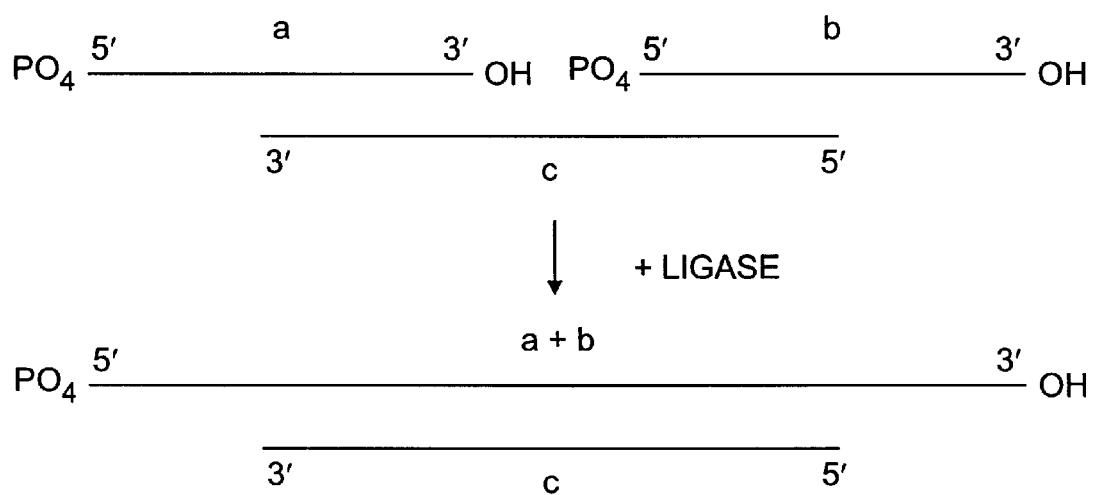

Releasing a set of oligonucleotides of known sequence from an oligomer-storing device This example, illustrated in FIGS. 5A and 5B, demonstrates an embodiment of the invention in which three selected DNA oligonucleotides, a, b, and c, are released from an oligomer storage device, and oligomers a and b are hybridized end-to-end to complementary oligomer c and are ligated together to produce a longer DNA molecule. This method is useful, for example, as a step in a protocol for solving a Hamiltonian path problem (Adleman et al., Supra, pages 1022–1023), or for making a synthetic gene.

The device that stores and releases the oligomers comprises a 1 cm×1 cm wafer of crystalline Al$_2$O$_3$ substrate ((1) in FIG. 5A) that supports a square array of 165×165 depot pads. Wafers of crystalline Al$_2$O$_3$, "synthetic sapphire", which are suitable for use with the present invention can be obtained from Saphikon, Milford, N.H., 03055. The top surface of each depot pad is 50 $\mu$m×50 $\mu$m, and the depot pads are spaced 10 $\mu$m apart in both x and y directions in the array. Each depot pad comprises 3 layers, (1) a thermally insulating 1 $\mu$m thick layer of porous SiO$_2$ which is attached to the Al$_2$O$_3$ substrate, (2) a light-absorbing 0.5 $\mu$m thick layer of amorphous SiO$_2$, and (3) a top, 0.5 $\mu$m thick layer of SiO$_2$, to which oligomers having selected nucleotide sequences are attached ((2) in FIG. 5A; see (10), (11), and (12) in FIG. 2). The attached oligomers are 20-mer DNA oligonucleotides (20 nucleotides in length) that are covalently attached at their 3' ends to uncharged spacer groups, which spacer groups are covalently attached to the upper SiO$_2$ surfaces of the depot pads. 20-mer DNA oligonucleotides which are complementary to the attached oligomers are stored in the device by their being specifically hybridized to the attached oligomers by Watson-Crick base-pairing. The stored oligonucleotides have 5'-phosphate and 3'-OH termini, so that they can be ligated together.

The depot array is immersed in about 100 $\mu$l of solution containing 1 M NaCl, 5 mM EDTA, 0.1 M Tris-Cl, pH 8.0, 0.5% SDS.

As shown in FIG. 5A, the depot sites storing oligonucleotides a, b, and c, are each irradiated through the Al$_2$O$_3$ substrate with approximately 100 milliwatts of argon laser light (488 nm) ((9) in FIG. 5A) to melt double-stranded oligonucleotide complexes at the heated depots and release the desired single-stranded DNA oligonucleotides molecules into the solution ((5) in FIG. 5).

The 3' half of oligomer a and the 5' half of oligomer b are complementary, respectively, to the 3' and 5' halves of oligomer c. Thus as shown in FIG. 5B, oligomer c hybridizes to the 3' end of oligomer a, and also to the 5' end of oligomer b, and it functions as a molecular splint by aligning the a and b oligomers end-to-end so that they can be covalently joined by ligase enzyme to produce a longer DNA molecule.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. A method for providing a set of oligomers comprising known subunit sequences comprising:
   a) obtaining a device for storing and providing oligomers comprising a substrate that supports an array of oligomer depots;
   wherein each depot comprises a delimited area or volume at which is attached a plurality of oligomers having a known subunit sequence, said oligomers being oligonucleotides and/or oligonucleotide analogs;
   wherein the subunit sequence of the oligomers attached to at least one of said depots is different from the subunit sequence of the oligomers attached to a different depot of said array; and
   wherein oligomers comprising known subunit sequences are stored at a plurality of depots of said array by being hybridized by Watson-Crick pairing to the oligomers attached at said depots to form double-stranded complexes, said stored oligomers also being oligonucleotides and/or oligonucleotide analogs;
   b) locally heating one or more selected depots of the intact array to denature double-stranded complexes of said selected depots and release oligomers stored therein, without effecting significant denaturation of double-stranded complexes of the unselected depots of the array; and
   c) collecting the oligomers released as a result of locally heating the selected depots.

2. The method of claim 1, wherein the oligomers attached to said depots and the oligomers that are hybridized to said attached oligomers are selected from the group consisting of DNA oligonucleotides, RNA oligonucleotides, DNA oligonucleotide analogs, and RNA oligonucleotide analogs.

3. The method of claim 1, wherein the oligomers attached to said depots and the oligomers that are hybridized to said attached oligomers are from 4 to 1000 subunits in length.

4. The method of claim 3, wherein the oligomers stored in the depots are about 8 to 30 subunits in length.

5. The method of claim 1, wherein the depot array comprises 2 to $10^7$ depots.

6. The method of claim 5, wherein the depot array comprises $10^2$ to $10^7$ depots.

7. The method of claim 1, wherein the depots are supported by a rigid substrate.

8. The method of claim 1 wherein the depot sites range in diameter from about 1 micron to about 1 centimeter.

9. The method of claim 1 wherein the depot sites are thermally isolated from each other.

10. The method of claim 1 wherein said selected depots are heated by irradiation from a radiant energy source or by application of electric current to electronic heating elements.

11. The method of claim 10 wherein two or more of said selected depots are heated serially.

12. The method of claim 10 wherein two or more of said selected depots are heated at the same time.

13. The method of claim 1, further comprising:
   d) allowing at least one of said oligomers from step c) to hybridize specifically to a complementary nucleotide sequence in a template nucleic acid, and contacting said hybridized oligomer with an enzyme with nucleic acid polymerase activity so that the hybridized oligomer is extended from its 3' end and a nucleic acid fragment complementary to a portion of the template nucleic acid is synthesized.

14. The method of claim 1, further comprising:
   d) allowing at least one of said oligomers from step c) to hybridize specifically to a complementary nucleotide sequence in a nucleic acid template molecule comprising a first nucleic acid fragment to be amplified which is positioned on the 3' side of said complementary nucleotide sequence;
   allowing at least one of said oligomers from step c) to hybridize specifically to a complementary nucleotide sequence in a nucleic acid template molecule comprising a second nucleic acid fragment to be amplified which is positioned on the 3' side of said complementary nucleotide sequence, and which is complementary to said first nucleic acid fragment to be amplified;
   contacting said hybridized oligomers with an enzyme with nucleic acid polymerase activity so that the hybridized oligomers are extended from their 3' ends and nucleic acids comprising said nucleic fragments to be amplified are synthesized;
   denaturing the resulting double-stranded nucleic acids, and repetitively carrying out said hybridization, polymerization, and denaturation steps to as to amplify said nucleic fragments to be amplified.

15. The method of claim 1, further comprising:

d) allowing at least one of said oligomers from step c) to hybridize specifically as a probe to a complementary nucleotide sequence in a target nucleic acid.

16. The method of claim 1, further comprising:

d) hybridizing at least two oligomer molecules from step c) end-to-end to adjacent, complementary nucleotide sequences in at least one splint nucleic acid, and covalently joining the 3'-OH end of at least one of the hybridized oligomers to the 5'-phosphorylated end of an adjacent hybridized oligomer by an enzyme with ligase activity.

17. The method of claim 1, further comprising:

d) using said oligomers from step c) to determine a solution to a mathematical problem that is solvable by DNA-based computation.

* * * * *

```
                         SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

TCTTAACATA GGAATTTGAG GCAGTACGCA AAAA                                     34

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

TGCGTACTGC CTCAAATTCC TATGTTAAGA                                          30

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

TGCGTACTGC CTCAAATTCC TATGTT                                              26

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

NNNNNCGAGA CTGCACT                                                        17
```

```
(2) INFORMATION FOR SEQ ID NO:5:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

AGTGCAGTCT CGA                                                      13

(2) INFORMATION FOR SEQ ID NO:6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

AGTGCAGTCT CGT                                                      13

(2) INFORMATION FOR SEQ ID NO:7:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

AGTGCAGTCT CGG                                                      13

(2) INFORMATION FOR SEQ ID NO:8:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

AGTGCAGTCT CGC                                                      13

(2) INFORMATION FOR SEQ ID NO:9:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

NNNGTCTCN                                                            9

(2) INFORMATION FOR SEQ ID NO:10:

(i) SEQUENCE CHARACTERISTICS:
        (A) LENGTH: 13 base pairs
```

(B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:10:

NNNNNGAGAC NNN                                                             13

(2) INFORMATION FOR SEQ ID NO:11:

(i) SEQUENCE CHARACTERISTICS:
          (A) LENGTH: 43 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:11:

TGCGTACTGC CTCAAATTCC TATGTTNNNN NCGAGACTGC ACT                             43

(2) INFORMATION FOR SEQ ID NO:12:

(i) SEQUENCE CHARACTERISTICS:
          (A) LENGTH: 47 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:12:

AGTGCAGTCT CGNTCTTAAC ATAGGAATTT GAGGCAGTAC GCAAAAA                         47

(2) INFORMATION FOR SEQ ID NO:13:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:13:

NTCTTAACAT AGGAATTTGA GGCAGTACGC AAAAA                                      35

(2) INFORMATION FOR SEQ ID NO:14:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:14:

TGCGTACTGC CTCAAATTCC TATGTTN                                               27

(2) INFORMATION FOR SEQ ID NO:15:

(i) SEQUENCE CHARACTERISTICS:
          (A) LENGTH: 12 base pairs
          (B) TYPE: nucleic acid
          (C) STRANDEDNESS: single
          (D) TOPOLOGY: linear -continued (ii) MOLECULE TYPE: DNA (xi) SEQUENCE DESCRIPTION: SEQ ID NO:15:

AGTGCAGTCT CG                                                                 12

(2) INFORMATION FOR SEQ ID NO:16:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

NNNNCGAGAC TGCACT                                                             16